US00PP29208P2

(12) United States Plant Patent
Stemkens

(10) Patent No.: US PP29,208 P2
(45) Date of Patent: Apr. 3, 2018

(54) ***LAVANDULA* PLANT NAMED 'LABZ0007'**

(50) Latin Name: *Lavandula stoechas*
Varietal Denomination: LABZ0007

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/330,274

(22) Filed: Sep. 1, 2016

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — Dale Skalla

(57) ABSTRACT

A new *Lavandula* plant named 'LABZ0007', particularly distinguished by numerous purple sterile large bracts, purple black flowers, medium green foliage without greyish hue, a strong sized plant with a rounded, mounding habit, early to flower and long flowering. The variety is also more winter hardy than normal for the species: minus 5 C is easily survived.

1 Drawing Sheet

Latin name of the genus and species of the plant claimed: *Lavandula stoechas.*

Varietal denomination: 'LABZ0007'.

BACKGROUND OF THE NEW PLANT

The present invention comprises a new *Lavandula*, botanically known as *Lavandula stoechas*, and hereinafter referred to by the variety name 'LABZ0007'.

'LABZ0007' is a product of a planned breeding program. The new cultivar has deep purple flowers and large, violet bracts, medium green foliage with very little greyish hue, small sized plant with a relatively upright plant habit, is early to flower and long flowering.

'LABZ0007' originated from a pollination made in 2009 in a greenhouse in Enkhuizen, The Netherlands. The female parent was the unpatented, proprietary plant designated 'G6114-1', with a lilac flower, strong habit, and starting to flower 3 weeks later when compared to 'LABZ0007'.

The male parent of 'LABZ0007' is the unpatented, proprietary plant designated 'N2966-51' with a purple flower, erect habit that is better winter hardy compared to 'LABZ0007'.

The resultant seed was sown in January 2011 and grown outdoors in Enkhuizen, The Netherlands. 'LABZ0007' was selected as a single flowering plant within the progeny of the stated cross on Jul. 3, 2011 in Enkhuizen, Netherlands.

The first act of asexual reproduction of 'LABZ0007' was accomplished when vegetative cuttings were propagated from the initial selection in September 2011 in a greenhouse in Enkhuizen, The Netherlands.

BRIEF SUMMARY OF INVENTION

Horticultural examination of plants grown from cuttings of the plant initiated September 2011, and continuing thereafter, has demonstrated that the combination of characteristics as herein disclosed for 'LABZ0007' are firmly fixed and are retained through successive generations of asexual reproduction.

'LABZ0007' has not been observed under all possible environmental conditions. The phenotype may vary significantly with variations in environment such as temperature, light intensity and day length.

'LABZ0007' has not been made publicly available prior to the effective filing date of this application, notwithstanding any disclosure that may have been made less than one year prior to the effective filing date of this application by the inventor or another who obtained 'LABZ0007' directly from the inventor.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawing shows typical flower and foliage characteristics of 'LABZ0007' with colors being as true as possible with an illustration of this type. The photographic drawing shows in FIG. 1 a flowering plant of the new variety.

DETAILED BOTANICAL DESCRIPTION

The plant descriptions and measurements were taken outdoors in Enkhuizen, The Netherlands on Jul. 14, 2016 on about 13 weeks old plants. Rooted cuttings had been planted into 13 cm pots in week 15 2016. The plants were not pinched.

The aforementioned photograph: FIG. 1 was taken in Enkhuizen, The Netherlands on Jul. 4, 2016 and showing a plant from an outdoor trial. The plant was about 13 weeks of age. Plants started flowering naturally by beginning of August.

Color references are made to The Royal Horticultural Society Colour Chart (R.H.S.) 2001.

TABLE 1

DIFFERENCES BETWEEN THE NEW VARIETY 'LABZ0007' AND A MOST SIMILAR VARIETY

| | 'LABZ0007' | 'LABZ0004' (U.S. Plant Pat. No. 27,493) |
|---|---|---|
| Plant size: | More upright | Bushy |
| Size of bracts: | 3 cm | 6 cm |
| Number of bracts per inflorescence: | 3 to 6 | 7 to 12 |
| Bract color: | RHS 86C | RHS N86C |

Plant:

*Plant spread.*—26 cm.

*Plant height.*—44 cm, to top of flowering plane 32 cm to top of foliar plane.

*Growth rate.*—Fast.

*Plant vigor.*—Robust.

*Length of primary lateral branches.*—25 cm.

*Diameter of lateral branches.*—0.3 cm.

*Quantity of lateral branches.*—30.

*Plant habit.*—Dense upright shape.

Stem:

*Juvenile color.*—RHS 137B.

*Mature color.*—RHS 137C.

*Texture/pubescence.*—Densely pubescent.

*Shape.*—Round.

*Strength.*—Very strong and flexible.

*Internode length.*—1.3-1.9 cm.

Propagation and roots:

*Time to initiate roots.*—About 7-10 days at 21 degrees C.

*Time to produce a rooted cutting.*—About 18-23 days at 21 degrees C.

*Root description.*—Fine, fibrous, developing a woody texture with age.

*Color.*—RHS 175B.

Foliage:

*Leaf.*—

*Arrangement.*—Opposite.

*Leaf type.*—Simple.

*Quantity.*—24 fully expanded per main branch and 27 juvenile leaves.

*Length.*—2.3 cm.

*Width.*—0.3 cm.

*Shape of blade.*—Lanceolate.

*Apex.*—Acute.

*Base.*—Truncate.

*Attachment.*—Sessile.

*Margin.*—Entire.

*Texture of all surfaces.*—Pubescent.

*Leaf fragrance.*—Very strong lavender scent with a hint of rosemary.

*Color.*—Young foliage upper side: RHS 137B. Young foliage under side: RHS 137C. Mature foliage upper side: RHS 137C. Mature foliage under side: RHS 137B.

*Venation.*—Reticulate.

*Venation color upper side.*—RHS 144A, only main vein distinguishable from foliage color.

*Venation color under side.*—RHS 145C.

*Petiole.*—Absent.

Inflorsecence:

*Blooming period.*—Late spring to mid-summer.

*Form and shape.*—Small single flower in verticillasters arranged in spikes. Most commonly 8 rows of flowers. Flowers have small bracts, and large showy terminal bracts. One flower spike per lateral stem.

*Number of individual flowers per spike.*—122.

*Fragrance.*—None.

*Flower lastingness.*—Individual flowers lasts 1-2 weeks, inflorescence remain ornamental for 6-8 weeks.

*Inflorescence size, excluding terminal bracts.*—Length: 5.0 cm. Width: 2.4 cm. Shape: Cylindrical.

Bud:

*Length.*—0.5 cm.

*Diameter.*—0.2 cm.

*Shape.*—Ovate.

*Color.*—RHS 77C.

*Rate of opening.*—Varies with climactic conditions: 3-7 days from colored bud to open flower.

Corolla:

*Corolla shape.*—Salverform.

*Petal number.*—5.

*Petals fused or unfused.*—Fused at base.

*Petal apex.*—Obtuse.

*Petal base.*—Fused.

*Petal shape.*—Top 2 lobes obovate, lower 3 lobes ovate.

*Petal margin.*—Entire.

*Petal surfaces.*—Glabrous.

*Length.*—0.3 cm (corolla tube).

*Diameter.*—0.2 cm.

*Coloration of individual flowers, excluding terminal bracts.*—Immature: RHS N89A darker. Mature: RHS N89A even darker.

Bracts:

*Bract shape.*—Elliptic.

*Bract apex.*—Acute with a cusp.

*Bract color.*—RHS 137B, cusp colored RHS 185B.

*Terminal bracts (sterile).*—Quantity: 4 large and 1 or 2 smaller per inflorescence.

Large (terminal) bracts:

*Length.*—3.0 cm.

*Width.*—1.0 cm.

*Form.*—Petaloid.

*Margin.*—Entire and undulating.

*Surface.*—Smooth.

*Appearance.*—Matte.

*Shape.*—Oblanceolate.

*Apex.*—Acute.

*Base.*—Attenuate.

*Vein pattern.*—Reticulate.

*Color.*—Upper side of immature bract: RHS N82B, base lighter, RHS N82C. Veins darker, RHS N78C. Under side of immature bract: RHS N82B Veins darker, RHS 77B. Upper side of mature bract: RHS N82A. Under side of mature bract: RHS N82A.

Small bracts:

*Quantity.*—Typically 2 or 3.

*Length.*—2.0 cm.

*Width.*—0.5 cm, unfolded.

*Apex.*—Bi-lobe.

*Margin.*—Entire.

*Base.*—Attenuate.

*Aspect*.—Undulating and folded inward at the mid-vein.

*Color*.—Upper side of immature bract: RHS N82B, base lighter, RHS N82C. Veins darker, RHS N78C. Under side of immature bract: RHS N82B Veins darker, RHS N82C. Upper side of mature bract: RHS N82B. Under side of mature bract: RHS N82B.

Calyx:

*Width*.—0.2 cm.

*Length*.—0.9 cm.

*Shape*.—Flattened tube.

*Color*.—RHS 144C.

Peduncle:

*Peduncle length*.—12-15 cm.

*Peduncle diameter*.—0.3 cm.

*Aspect*.—Upright.

*Color*.—RHS 137B.

*Texture*.—Densely pubescent.

Reproductive organs:

*Androecium*.—Stamens: 4. Anther length: 0.05 cm. Anther color: RHS N155A. Pollen quantity: Pollen production not observed.

*Pistil*.—Number: 1. Length: 0.4 cm.

*Style*.—Length: 0.3 cm. Color: RHS N155A.

*Stigma*.—Length: 0.05 cm. Color: RHS N77C.

*Ovary*.—Minute and immeasurable.

Other characteristics:

*Seeds and fruits*.—Seed production not observed to date.

*Disease/pest resistance*.—Neither resistance nor susceptibility to the normal diseases and pests of *Lavandula stoechas* has been observed.

*Drought tolerance and cold tolerance*.—Hardy perennial. Tolerates high temperature to at least 36 degrees C. Tolerates low temperatures to degrees minus 5 C. While specific drought tolerance has not been observed, once plants are established very little water is necessary to maintain plants.

What is claimed is:

1. A new and distinct cultivar of *Lavandula* plant named 'LABZ0007', as substantially illustrated and described herein.

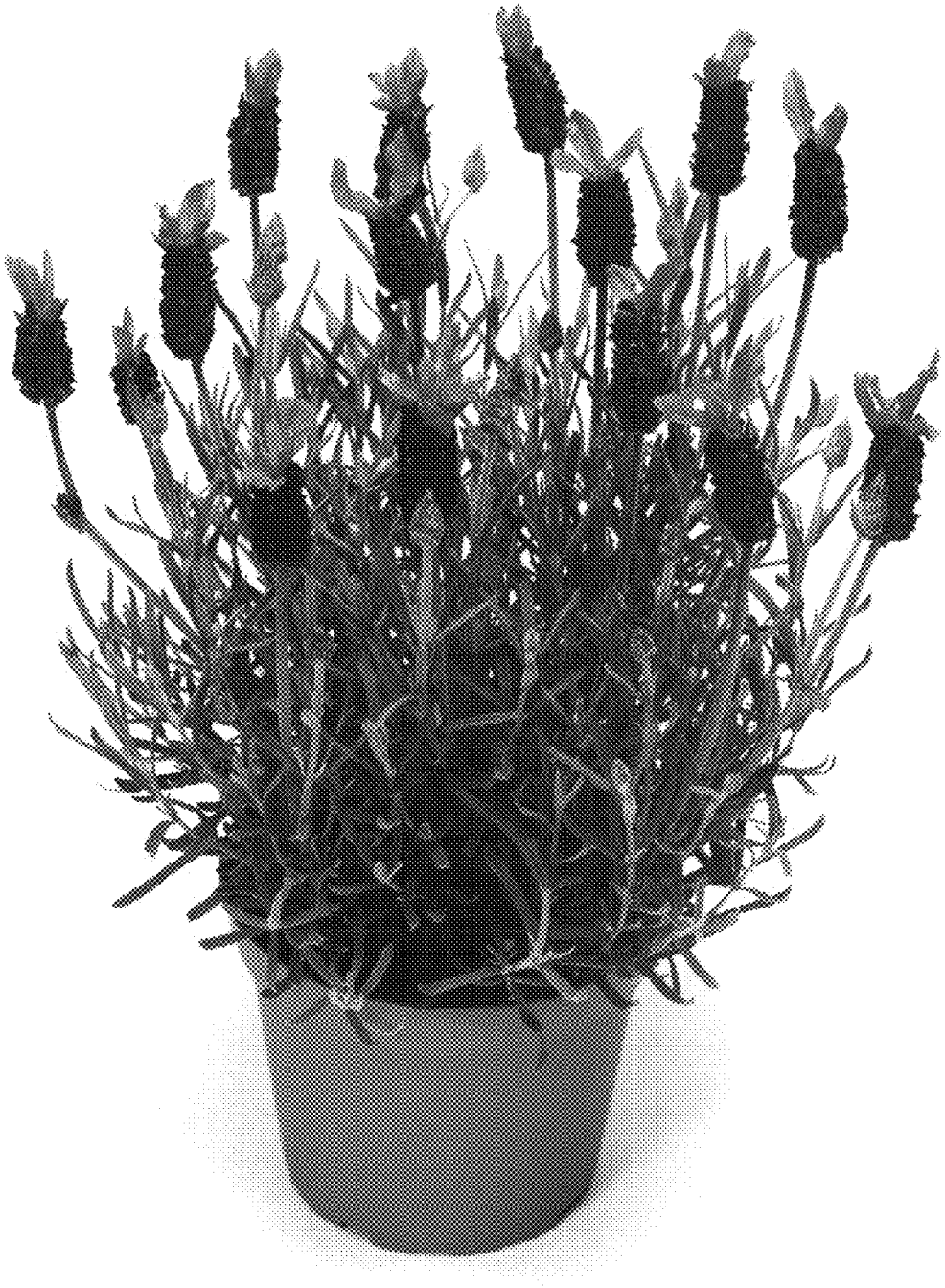

* * * * *